US005922602A

United States Patent [19]
Kumagai et al.

[11] Patent Number: 5,922,602
[45] Date of Patent: *Jul. 13, 1999

[54] CYTOPLASMIC INHIBITION OF GENE EXPRESSION

[75] Inventors: Monto Hiroshi Kumagai, Davis; Guy Richard della-Cioppa, Vacaville; Jonathan Donson, Davis; Damon Alan Harvey; Laurence K. Grill, both of Vacaville, all of Calif.

[73] Assignee: Biosource Technologies, Inc., Vacaville, Calif.

[ * ] Notice: This patent is subject to a terminal disclaimer.

[21] Appl. No.: 08/260,546

[22] Filed: Jun. 16, 1994

Related U.S. Application Data

[63] Continuation-in-part of application No. 08/184,237, Jan. 19, 1994, Pat. No. 5,589,367, which is a continuation of application No. 07/923,692, Jul. 31, 1992, Pat. No. 5,316,931, which is a continuation-in-part of application No. 07/600,244, Oct. 22, 1990, abandoned, and a continuation-in-part of application No. 07/641,617, Jan. 16, 1991, abandoned, and a continuation-in-part of application No. 07/737,899, Jul. 26, 1991, abandoned, and a continuation-in-part of application No. 07/739,143, Aug. 1, 1991, said application No. 07/600,244, is a continuation of application No. 07/310,881, Feb. 17, 1989, abandoned, which is a continuation-in-part of application No. 07/160,766, Feb. 26, 1988, abandoned, and a continuation-in-part of application No. 07/160,771, Feb. 26, 1988, abandoned, said application No. 07/641,617, is a continuation of application No. 07/347,637, May 5, 1989, abandoned, said application No. 07/737,899, said application No. 07/363,138, Jun. 8, 1989, abandoned, is a continuation-in-part of application No. 07/219,279, Jul. 15, 1988, abandoned.

[51] Int. Cl.$^6$ ............... C12N 15/83; C12N 5/10; C12N 15/63
[52] U.S. Cl. ............. 435/468; 435/320.1; 435/419
[58] Field of Search ................. 435/320.1, 410, 435/69.1, 419; 514/44

[56] References Cited

U.S. PATENT DOCUMENTS

| 5,107,065 | 4/1992 | Shewmaker et al. | 800/298 |
|---|---|---|---|
| 5,190,931 | 3/1993 | Inouye | 435/91.32 |
| 5,231,020 | 7/1993 | Jorgensen et al. | 800/281 |
| 5,272,065 | 12/1993 | Inouye et al. | 435/91.1 |
| 5,316,930 | 5/1994 | Loesch-Fries et al. | 800/280 |
| 5,316,931 | 5/1994 | Donson et al. | 800/288 |
| 5,453,566 | 9/1995 | Shewmaker et al. | 800/286 |

FOREIGN PATENT DOCUMENTS

| A 0 425 004 | 5/1991 | European Pat. Off. . |
|---|---|---|
| WO A 90 12107 | 10/1990 | WIPO . |
| WO A 91 09128 | 6/1991 | WIPO . |
| WO A 91 13078 | 9/1991 | WIPO . |
| WO A 91 13994 | 9/1991 | WIPO . |
| WO 93/03161 | 2/1993 | WIPO . |

OTHER PUBLICATIONS

Rothstein, Steven J. et al. "Stable and heritable inhibition of the expression of noplaine synthase in tobacco expressing antisense RNA". *Proceedings of the National Academy of Sciences*, USA 84:8439–8443 (1987).

Smith, C.J.S. et al. "Antisense RNA inhibition of polygalacturonase gene expression in transgenic tomatoes". *Nature* 334: 724–726 (1988).

Jorgensen, Richard. "Altered gene expression in plants due to trans interactions between homologous genes". *Tibtech*, vol. 8: 340–344 (1990).

Grierson, Don et al. "Does co–suppression of sense genes in transgenic plants involve antisense RNA?" *Tibtech* vol. 9: 122–123 (1991).

Bird, Colin R. et al. "Using Antisense RNA To Study Gene Function: Inhibition Of Carontenoid Biosynthesis In Transgenic Tomatoes". *Bio/Technology*, vol. 9: 635–639 (1991).

Bartley, Glenn E. et al. "Molecular cloning and expression in photosynthetic bacteria of a soybean cDNA coding for phytoene desaturase, an enzyme of the carotenoid biosynthesis pathway". *Proceedings of the National Academy of Sciences*, USA 88: 6532–6536 (1991).

Bartley, Glenn E. et al. "A Tomato Gene Expressed during Fruit Ripening Encodes an Enzyme of the Carotenoid Biosynthesis Pathway". *The American Society for Biochemistry and Molecular Biology, Inc.*, vol. 267, No. 8: 5036–5036 (1992).

Donson, J. et al. "Systemic expression of a bacterial gene by a tobacco mosaic virus–based vector". *Proceedings of the National Academy of Sciences*, USA, vol. 88: 7204–7208 (1991).

(List continued on next page.)

*Primary Examiner*—Terry McKelvey
*Attorney, Agent, or Firm*—Albert P. Halluin; Howrey & Simon

[57] ABSTRACT

The invention provides novel genetic constructions for the expression of inhibitory RNA in the cytoplasm of eukaryotic cells. The inhibitory RNA may be an anti-sense RNA or a co-suppressor RNA, and functions to reduce the expression of a gene of interest in the target cell. The genetic constructions of the invention are capable of replicating in the cytoplasm of a eukaryotic cell and comprise a promoter region in functional combination with an encoding polynucleotide. The genetic constructions may be designed so as to replicate in the cytoplasm of plant cells, yeast cells, and mammalian cells. When the eukaryotic cell of interest is a plant cell, the genetic construction is preferably derived from a plant RNA virus. Plant RNA virus derived genetic constructions may employ a plant virus subgenomic promoter, including subgenomic promoters from tobamoviruses in functional combination with the RNA encoding region. In a preferred embodiment of the invention, plant cells are induced to produce elevated levels of the carotenoid phytoene. The elevated levels of phytoene are achieved by inhibiting the expression of the enzyme phytoene desaturase using the vectors of the invention.

15 Claims, 2 Drawing Sheets

OTHER PUBLICATIONS

Pecker, Iris et al. "A single polypeptide catalyzing the conversion of phytoene to 5-carotene is transcriptionally regulated during tomato fruit ripening". *Proceedings of the National Academy of Sciences*, USA vol. 89: 4962–4966 (1992).

Gray, Julie et al. "Molecular biology of fruit ripening and its manipulation with antisense genes". *Plant Molecular Biology* 19: 69–87 (1992).

Scolnik, Pablo and Bartley Glenn E. "Phytoene Desaturase fron *Arabidopsis*". *Plant Physiology* 103: 1475 (1993).

Giullano, Giovanni et al. "Regulation of Carotenoid Biosynthesis during Tomato Development". *The Plant Cell*, vol. 5:379–387 (1993).

Dogbo, Odette et al. "Carotenoid biosynthesis: Isolation and characterization of a bifunctional enzyme catalyzing the synthesis of phytoene". *Proceedings of the National Academy of Sciences*, USA 85: 7054–7058 (1988).

van der Krol, Alexander R. et al. "An anti-sense chalcone synthase gene in transgenic plants inhibits flower pigmentation". *Nature* 333: 866–869 (1988).

Kumagai, et al., 1995, "Cytoplasmic inhibition of carotenoid biosynthesis with virus–derived RNA," *Proc. Nat. Acad. Sci. USA* 92(5): 1679–1683.

Powers et al., 1944, "Intracellular Immunization of Mosquito Cells to LaCrosse Virus Using a Recombinant Sindbis Virus Vector," *Virus Research* 32(1):57–67.

Misawa et al., 1993, "Functional expression of the *Erwinia uredovora* carotenoid biosynthesis gen ctrl in transgenic plants showing an increase of beta–carotene biosynthesis activity and resistance to the bleaching herbicide norflurazon," *The Plant Journal* 4(5):833–840.

Bramley et al., 1992, "Biochemical Characterization of Transgenic Tomato Plants in Which Carotenoid Synthesis has been Inhibited Through the Expression of Antisense RNA to pTOM5," *The Plant Journal* 2(3):343–349.

Hayes et al., 1988, "Gene amplification and expression in plants by a replicating geminivirus vector," *Nature* 334:179–182.

Lehto et al, Virology, 1990, vol. 175: pp. 30–40.

Stein et al, Science, Aug. 20, 1993, vol. 261: pp. 1004–1011.

French et al, Science, Mar. 14, 1986, vol. 231, pp. 1294–1297.

Helene et al, Biochem. et Biophys Acta, 1990,. vol. 1049: pp. 99–125.

```
PDS-Nb   ATAAACCCTGACGAGCTTTCGATGCAGTGCATCTTGATTGCTTTGAACAG   50
         |||||||||||||| ||||| ||||||||||| ||| | ||||||||||
PDS-Le   ATAAACCCTGACGAACTTTCAATGCAGTGCATTTTGATCGCATTGAACAG   50

PDS-Nb   ATTTCTTCAGGAGAAACATGGTTCAAAAATGGCCTTTTTAGATGGTAACC   100
          ||||||||||||||||||||||||||||||||||||||||||||||| |
PDS-Le   GTTTCTTCAGGAGAAACATGGTTCAAAAATGGCCTTTTTAGATGGTAATC   100

PDS-Nb   CTCCTGAGAGACTTTGCATGCCGATTGTGGAACATATTGAGTCAAAAGGT   150
         ||||||||||||||||||||||||||||| ||||| |||||||||||||
PDS-Le   CTCCTGAGAGACTTTGCATGCCGATTGTTGAACACATTGAGTCAAAAGGT   150

PDS-Nb   GGCCAAGTCAGACTAAACTCACGAATAAAAAAGATCGAGCTGAATGAGGA   200
         |||||||||||||| |||||||||||||||||||| ||||||||||||
PDS-Le   GGCCAAGTCAGACTGAACTCACGAATAAAAAAGATTGAGCTGAATGAGGA   200

PDS-Nb   TGGAAGTGTCAAATGTTTTATACAGAATAATGGCAGTACAATTAAAGGAG   250
         |||||||||||| ||||||||| |||| ||| |||||||| | ||||||
PDS-Le   TGGAAGTGTCAAGAGTTTTATACTGAGTGACGGTAGTGCAATCGAGGGAG   250

PDS-Nb   ATGCTTTTGTGTTTGCCACTCCAGTGGATATCTTGAAGCTTCTTTTGCCT   300
         ||||||||||||||||| |||||||||||| | ||||||||||| ||||
PDS-Le   ATGCTTTTGTGTTTGCCGCTCCAGTGGATATTTTCAAGCTTCTATTGCCT   300

PDS-Nb   GAAGACTGGAAAGAGATCCCATATTTCCAAAAGTTGGAGAAGCTAGTGGG   350
         |||||||||||||||| | ||||||||||||||||||||||| ||| ||
PDS-Le   GAAGACTGGAAAGAGATTCCATATTTCCAAAAGTTGGAGAAGTTAGTCGG   350

PDS-Nb   AGTTCCTGTGATAAATGTCCATATATGGTT   380
         ||| ||||||||||||||| ||||||||||
PDS-Le   AGTACCTGTGATAAATGTACATATATGGTT   380
```

FIG. 2

CYTOPLASMIC INHIBITION OF GENE EXPRESSION

RELATED APPLICATIONS

This application is a continuation-in-part of U.S. patent application Ser. No. 08/184,237, filed Jan. 19, 1994, now issued as U.S. Pat. No. 5,589,367, which is a continuation of U.S. application Ser. No. 07/923,692, filed Jul. 31, 1992, now issued as U.S. Pat. No. 5,316,931, on May 31, 1994, which is a continuation-in-part of U.S. application Ser. No. 07/600,244, filed Oct. 22, 1990, now abandoned ("the '244 application"), U.S. application Ser. No. 07/641,617, filed Jan. 16, 1991, now abandoned ("the '617 application"), U.S. application Ser. No. 07/737,899, filed Jul. 26, 1991, now abandoned ("the '899 application"), and U.S. application Ser. No. 07/739,143, filed Aug. 1, 1991, now abandoned ("the '143 application"), the '244 application is a continuation of U.S. application Ser. No. 07/310,881, filed Feb. 17, 1989, now abandoned, which is a continuation-in-part of U.S. application Ser. No. 07/160,766, filed Feb. 26, 1988, now abandoned, and U.S. application Ser. No. 07/160,771, filed Feb. 26, 1988, now abandoned, the '617 application is a continuation of U.S. application Ser. No. 07/347,637, filed May 5, 1989, now abandoned, and the '899 application is a continuation of U.S. application Ser. No. 07/363,138, filed Jun. 8, 1989, now abandoned, which is a continuation-in-part of U.S. application Ser. No. 07/219,279, filed Jul. 15, 1988, now abandoned.

FIELD OF THE INVENTION

This invention is in the field of gene regulation through anti-sense RNA endogenously produced inhibitory RNA molecules such as anti-sense RNA and co-suppressor RNA.

BACKGROUND

One of the primary goals of genetic engineering has been to control the expression of selected genes in eukaryotic organisms of interest. While it has been relatively straightforward to insert new genes for expression into eukaryotic cells, the targeting of endogenous genes for reduced expression has been more difficult to achieve. Site-directed inactivation of genes in higher organisms has required extremely complex genetic manipulations and is not applicable to a wide range of organisms. One method reducing the expression of specific genes in eukaryotic organisms has been through the use of anti-sense RNA and through co-suppression.

Anti-sense RNA has been used to reduce the expression of pre-selected genes in both plants and animals. Descriptions of the use of anti-sense RNA to reduce the expression of selected genes in plants can be found, among other places in U.S. Pat. No. 5,107,065, Smith et al. *Nature* 334: 724–726 (1988), Van der Krol et al., *Nature* 333: 866–869 (1988), Rothstein et al., *Proc. Natl. Aca. Sci. USA* 84:8439–8443 (1987), Bird et al., *Bio/Technology* 9:635–639 (1991), Bartley et al. *Biol. Chem.* 267:5036–5039 (1992), and Gray et al., *Plant Mol. Bio.* 19:69–87 (1992).

Another method of reducing the expression of specific genes in eukaryotic organisms is through the use of co-suppressor RNA. Co-suppressor RNA, in contrast to anti-sense RNA, is in the same orientation as the RNA transcribed from the target gene, i.e., the "sense" orientation.

It is possible that biochemical pathways in plants transfected with hybrid viruses could be altered by overproducing an enzyme involved in a rate-limiting step, or by inhibiting the synthesis of an enzyme via antisense RNA. Although the expression of numerous genes in transgenic plants have been repressed by antisense RNA, the actual mechanism and location of inhibition is not known. In the nucleus, antisense RNA may directly interfere with transcription or form duplexes with the heterogeneneous nuclear (hnRNA). There is evidence that inhibition of endogenous genes can occur in transgenic plants containing sense RNA A. R. van der Krol et al., *Nature* 333:866–869 (1988) and C. Napoli et al., *Plant Cell* 2:279–289 (1990) mechanism of this down regulation or "co-suppression" is thought to be caused by the production of antisense RNA by read through transcription from distal promoters located on the opposite strand of the chromosomal DNA (Greison, et al. *Trends in Biotech.* 9:122–123 (1991)). Alternatively, in the cytoplasm, antisense RNA may form a double-stranded molecule with the complimentary mRNA and prevent the translation of mRNA into protein.

Tobamoviruses, whose genomes consist of one plus-sense RNA strand of approximately 6.4 kb, replicate solely in the cytoplasm, and can be used as episomal RNA vectors to alter plant biochemical pathways. Hybrid tobacco mosaic (TMV)/odontoglosum ringspot viruses (ORSV) have been used previously to express heterologous enzymes in transfected plants (Donson, et al. *Proc. Natl. Aca. Sci. USA* 88:7204 (1991) and Kumagai, et al. *Proc. Natl. Aca. Sci USA* 90:427–430 (1993), minus-Sense RNA Strand, (Miller, et al.). Infectious RNA transcripts from viral cDNA clones encode proteins involved in RNA replication, movement, and encapsidation (10). Subgenomic RNA for messenger RNA synthesis is controlled by internal promoters located on the minus-sense RNA strand (*N.benthamiana* plants were inoculated with in vitro transcripts as described previously [W. O. Dawson, et al., *Proc. Natl. Acad. Sci. U.S.A.* 83, 1832 (1986)]). Insertion of foreign genes into a specific location under the control of an additional subgenomic RNA promoter have resulted in systemic and stable expression of neomycin phosphotransferase and α-trichosanthin (Donson, et al. *Proc. Natl. Aca. Sci. USA* 88:7204 (1991) and Kumagai, et al. *Proc. Natl. Aca. Sci USA* 90:427–430 (1993)).

One of the many biochemical pathways that could serve as a target for genetic manipulation is the biosynthesis of carotenoids. On the first committed step in carotenoid biosynthesis in higher plants is the condensation of two geranylgeranyl pyrophosphate molecules to phytoene, a colorless $C_{40}$ hydrocarbon, by the enzyme phytoene synthase. In the ripening fruit of *Lycopersicon esculentum*, phytoene synthase is a monomeric, chloroplast localized protein with an approximate relative molecular mass of 42 kDa. This enzyme is initially synthesized as a 47-kDa preprotein and is processed by the removal of a transit peptide during import to the chloroplast (Bartley, et al. *J. Biol. Chem.* 267:5036–5039 (1992)). Transgenic tomato plants containing anti-sense to phytoene synthase mRNA produce yellow fruit and pale flowers. Although the fruit specific carotenes are reduced by 97%, the levels of carotenoids in the leaves of the transgenic plants are unaffected, (Bird, et al., *Bio/Technology* 9:635–639 (1991)). It has been proposed that an additional set of biosynthetic genes occurs in plants which regulate the expression of leaf specific carotenoids.

The subsequent step in the biosynthetic pathway is the modification of the colorless phytoene to phytofluene and ζ-carotene by phytoene desaturase. Among higher plants, the isolation of gene encoding this enzyme has been described for tomato, Pecker, et al., *Proc. Natl. Acad. Sci. U.S.A.*, 89, 4962 (1992), and *Arabidopsis thaliana* (Scolnick and Bartley, *Plant Physiol* 103:147 (1993)). Phytoene desaturase is inhibited by norflurazon, a bleaching herbicide, in a reversible, non-competitive manner (Sandman, et al., *Target Sites of Herbicide Actions*, G. Sandman, P. Boger Es. (RC press, Boca Rotan (1989)). Application of this compound causes a dramatic decrease in leaf carotenoids and chlorophylls and a subsequent accumulation of phytoene. The reduction of the photoprotective carotenoids derived from phytoene may cause a rapid destruction of chlorophyll by photooxidation.

The need for new methods of reducing the expression of specific genes in eukaryotes is clearly established. The invention described herein provides new methods for reducing the expression of selected genes, genetic constructions for practicing the methods, and cells transformed by these genetic constructions, and higher organisms comprising the transformed cells.

SUMMARY OF THE INVENTION

One aspect of the invention is to provide novel genetic constructions for the expression of inhibitory RNA in the cytoplasm of eukaryotic cells. The genetic constructions of the invention are capable of replicating in the cytoplasm of a eukaryotic cell and comprise a promoter region in functional combination with an inhibitory RNA encoding polynucleotide, i.e., encoding an anti-sense RNA or a co-suppressor RNA. The genetic constructions of the invention may be designed so as to replicate in the cytoplasm of plant cells, yeast cells, or mammalian cells. When the eukaryotic cell of interest is a plant cell, the genetic construction is preferably derived from a plant RNA virus, more preferably a positive single-stranded RNA virus. Plant RNA virus derived genetic constructions may comprise a plant virus subgenomic promoter, including subgenomic promoters from tobamoviruses, in functional combination with the inhibitory RNA encoding region.

Another aspect of the invention is to provide cells comprising the genetic constructions of the invention and to provide organisms comprising a plurality of such cells.

Another aspect of the invention is to provide methods of reducing the expression of a gene of interest in eukaryotic cells, i.e., methods of producing eukaryotic cells exhibiting reduced levels of expression of a gene of interest. The methods of the invention comprise the step of transforming a cell with a genetic construction of the invention in which the inhibitory RNA encoding region is specific for the gene of interest. Another aspect of the invention is to provide plant cells that produce elevated levels of the carotenoid phytoene. The elevated levels of phytoene are achieved by inhibiting the expression at the enzyme phytoene desaturase using the vectors of the invention.

BRIEF DESCRIPTION OF THE FIGURES

FIG. 2. Nucleotide sequence comparison of *N. benthamiana* leaf phytoene desaturase (PDS1-Nb) (SEQ ID NO:14) and tomato phytoene desaturase (PDS-Le) (SEQ ID NO:15). The nucleotides are aligned to maximize sequence similarity.

DESCRIPTION OF THE SPECIFIC EMBODIMENTS

Definitions

Figure 1:
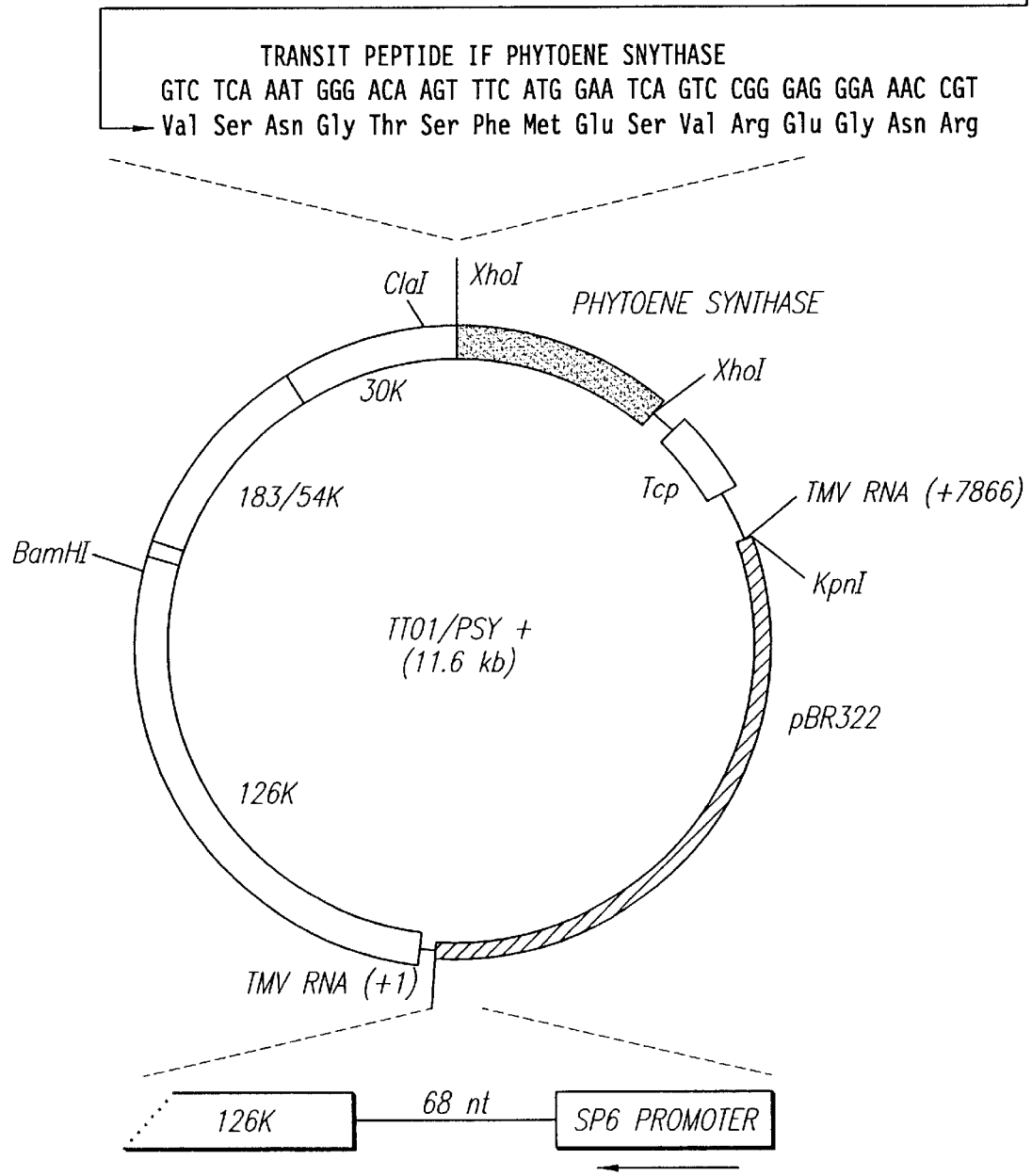
FIG. 1. Phytoene expression vector TTO1/PSY+. This plasmid contains the TMV-U1 126-, 183-, and 30-kDa ORFs, the ToMV coat protein gene (ToMVcp), the SP6 promoter, the tomato phytoene synthase gene, and part of the pBR322 plasmid. The TAA stop codon in the 30-kDa ORF is underlined. The TMV-U1 subgenomic promoter located within the minus strand of the 30-kDa ORF controls the expression of phytoene synthase. The putative transcription start point (tsp) of the subgenomic RNA is indicated with a period (.). A portion of the N terminal amino acid sequence of phytoene synthase (SEQ ID NO:11) is given. The DNA sequence encoding this portion of the plasmid is also given (SEQ ID NO:10).

The term "inhibitory RNA", as used herein, refers to an RNA molecule that interferes with the expression of a target gene. An "inhibitory RNA" is specific for one or more target genes. An inhibitory RNA may be an anti-sense RNA with respect to an RNA molecule transcribed from the target gene. Alternatively, the target gene inhibitory RNA may be a co-suppressor RNA with respect to an RNA molecule transcribed from the target gene.

The term "anti-sense RNA" as used herein, refers to an RNA molecule that is capable of forming a duplex with a second RNA molecule. Thus a given RNA molecule is said to be an anti-sense RNA molecule with respect to a second, complementary or partially complementary RNA molecule, i.e., the target molecule. An anti-sense RNA molecule may be complementary to a translated or an untranslated region of a target RNA molecule. The anti-sense RNA need not be perfectly complementary, to the target RNA. Anti-sense RNA may or may not be the same length of the target molecule; the anti-sense RNA molecule may be either longer or shorter than the target molecule.

The term "co-suppressor RNA" refers to an RNA molecule that effects suppression of expression of a target gene where the RNA is partially homologous to an RNA molecule transcribed from the target gene. A co-suppressor RNA molecule is the RNA molecule that effects co-suppression as described in U.S. Pat. No. 5,231,020, Krol et al., *Biotechniques* 6:958–976 (1988), Mol et al., *FEBS Lett.* 268:427–430 (1990), and Grierson, et al. *Trends in Biotech.* 9:122–123 (1991) and similar publications. A "co-suppressor" RNA is in the sense orientation with respect to the target gene, i.e., the opposite orientation of the anti-sense orientation.

The term "inhibitory RNA encoding polynucleotide" as used herein, refers to a polynucleotide, e.g., DNA, RNA, and the like, capable of being transcribed, when in functional combination with a promoter, so as to produce an inhibitory RNA molecule, e.g., an anti-sense RNA or a co-supressor RNA. Anti-sense RNA encoding polynucleotides and co-supressor encoding polynucleotides are both embodiments of the inhibitory RNA encoding polynucleotides. When the inhibitory RNA is an anti-sense RNA, the inhibitory RNA transcribed from the inhibitory RNA encoding polynucleotide region of the genetic constructions of the invention is preferably perfectly complementary to the entire length of the RNA molecule or molecules for which the anti-sense RNA is specific, i.e., the target. The anti-sense RNA encoding polynucleotide in the subject vectors may encode an anti-sense RNA that forms a duplex with a non-translated region of an RNA transcript such as an intron region, or 5' untranslated region, a 3' untranslated region, and the like. Similarly, a co-suppressor encoding polynucleotide in the subject vectors may encode an RNA that is homologous to translated or untranslated portions of a target RNA. An anti-sense RNA encoding polynucleotides may be conveniently produced by using the non-coding strand, or a portion thereof, of a DNA sequence encoding a protein of interest.

The term "reduced expression," as used herein, is a relative term that refers to the level of expression of a given gene in a cell produced or modified by the claimed methods as compared with a comparable unmodified cell, i.e., a cell lacking the subject vector, under a similar set of environmental conditions. Thus, a cell modified by the subject methods, i.e., a cell having "reduced expression" of the gene of interest, may express higher levels of that gene under a first set of environmental conditions, than a comparable unmodified cell under a second set of environmental conditions, if the second set of conditions is highly favorable to gene expression.

The Invention

The invention described herein exploits the discovery that RNA can reduce the expression of a target gene through inhibitory RNA interactions with target mRNA that take place in the cytoplasm of a eukaryotic cell, rather than in the nucleus. Prior to the invention, it was not known if inhibitory RNA reduced gene expression by means of an interaction that takes place in the cytoplasm or an interaction that takes place in the nucleus. Thus, prior to the invention, it was necessary to produce inhibitory RNA in the nucleus so as to be certain that inhibition would be achieved. Furthermore, it was not known if adequate concentrations of inhibitory RNA could be provided in the cytoplasm. Cytoplasmic expression of inhibitory RNA (specific for target genes) has numerous advantages over nuclear expression, these advantages include the ability to use high level expression vectors that are not suitable for nuclear expression. The use of such vectors is particularly advantageous in plants, because vectors capable of systemically infecting plants may be used to produce the inhibitory RNA. The invention described herein has many aspects. These aspects include novel genetic constructions for the expression of target gene inhibitory RNA in the cytoplasm of eukaryotic cells, cells transfected with these genetic constructions, multicellular organisms comprising the transfected cells, and methods for reducing the expression of selected genes in a cell by transforming a cell with a genetic construction of the invention.

There are numerous ways to produce the genetic constructions of the invention. Techniques for manipulating polynucleotides, e.g., restriction endonuclease digestion and ligation, are well known to the person of ordinary skill in the art. These conventional polynucleotide manipulation techniques may be used to produce and use the genetic construction of the invention. While some optimization of standard techniques may be employed to produce the subject genetic constructions, significant experimentation is not required to produce the genetic constructions or practice the claimed methods.

The genetic constructions of the invention comprise a promoter region in functional combination with an inhibitory RNA encoding polynucleotide. The promoter region is selected so as to be capable of driving the transcription of a polynucleotide sequence in a host cell of interest. Thus for example, when the eukaryotic cell is a plant cell, the promoter is selected so as to be able to drive transcription in plant cells. Promoters capable of functioning in a given eukaryotic cell are well known to the person of ordinary skill in the art. Examples of promoters capable of driving transcription in a cell of interest can be found, among other places in, Goeddel et al., *Gene Expression Technology Methods in Enzymology* Volume 185, Academic Press, San Diego, (1991), Ausubel et al, *Protocols in Molecular Biology,* Wiley Interscience (1994), and similar publications. When the cell for transformation is a plant cell, the RNA virus subgenomic promoters are preferably used as promoter regions. RNA virus subgenomic promoter are described, among other places in Dawson and Lehto, *Advances in Virus Research,* 38:307–342, PCT published application WO93/03161.

The genetic constructions of the invention are capable of replication or maintenance, at least transiently, in the cytoplasm of eukaryotic cells of interest i.e., a base vector. Thus, the genetic constructions of the invention necessarily comprise a polynucleotide region derived from a vector capable of being replicated or stably maintained in eukaryotic cell of interest. Many vectors capable of replication (or stable maintenance) in different types of eukaryotic cells are known. For example, vectors for use in yeast cells include 2μ circle derived vectors. Information describing vectors yeast and their use in yeast can be found, among other places, in Goeddel, et al. supra, Ausubel et al., supra, and similar publications.

Vectors for use in mammalian cells include bovine papilloma virus derived vectors, vaccinia derived vectors, semi-liki forrest virus vectors and the like. Information describing mammalian cell vectors and their use in mammalian cells can be found, among other places is Goedd, et al. supra, and Ausubel et al., supra. Vectors for use in plants include vectors derived from cauliflower mosaic virus, tobacco mosaic virus, tomato mosaic virus, and the like. Information describing plant cell vectors and their use in plant cells can be found, among other places, in PCT application WO93/03161, and Donson, et al. *Proc. Natl. Acad. Sci. USA,* 88:7204–7208 (1991).

The promoter driving transcription of the inhibitory RNA encoding region of the subject genetic constructions may be selected so as have a level of transcriptional activity sufficient to achieve the desired degree of expression of the target gene inhibitory RNA of interest. The promoter may be native or heterologous to the cell for genetic modification. The promoter may also be native or heterologous to the base vector, i.e., the portion of the vector other than the promoter and the inhibitory RNA encoding region. The promoter may be inducible or constitutive. Preferably, strong promoters are used to drive transcription of the inhibitory RNA encoding polynucleotide when the target RNA is highly expressed.

The invention also provides methods of reducing the expression of a gene or genes of interest in a eukaryotic cell. As a consequence of providing the subject methods of reducing gene expression in eukaryotic cell, the subject invention also provides methods of producing a eukaryotic cell having reduced expression of a gene of interest and eukaryotic cells that have reduced expression of a gene of interest, as produced by the methods of the invention. Reduction of gene expression is achieved by introducing one or more of the vectors of the invention into a eukaryotic cell. The vector used to transform the cell of interest comprises an inhibitory RNA encoding polynucleotide that encodes an inhibitory RNA specific for the gene for which reduced expression is sought. The method of reducing expression of the gene of interest comprises the step of introducing the subject genetic vector into a host cell that is capable of expressing the gene of interest under certain environmental conditions. The vector may be introduced into a cell of interest by any of a variety of well known transformation methods. Such methods include: infection, transfection, electroporation, ballistic projectile transformation, conjugation, and the like. The inventive aspect of the subject methods is not dependent upon the particular means by which the inhibitory RNA encoding vector is introduced into the cell of interest. The particular methods of introducing the vector into a cell of interest is, in part, dependent upon the particular cell for modification and the precise type of vector selected.

When the eukaryotic cells of interest for genetic modification by the subject vectors are plant cells, the vectors are preferably derived from RNA plant viruses. Preferred RNA plant virus vectors are positive strand single stranded RNA viruses. RNA plant virus vectors may be conveniently manipulated and introduced into cells in a DNA form instead of working directly with RNA vectors. Viral vector derived from tobamoviruses are particularly preferred. Descriptions of suitable plant virus vectors that may be modified so as to contain an inhibitory RNA encoding region in functional combination with a promoter as well as how to make and use such vectors, can be found in, among other places, PCT publication WO 93/03161, Kumagai et al, *Proc. Natl. Aca. Sci. USA* 90:427–430 (1993).

The invention also provides polynucleotides encoding phytoene synthase and phytoene desaturase, as well as various vector for the expression of target gene inhibitory RNA specific for phytoene synthase genes or phytoene desaturase genes. The first committed step in carotenoid biosynthesis in higher plants is the condensation of two geranylgeranyl pyrophosphate molecules to phytoene, a colorless $C_{40}$ hydrocarbon, by the enzyme phytoene synthase. The subsequent step in the biosynthetic pathway is the modification of the colorless phytoene to phytofluene and ζ-carotene by phytoene desaturase.

The invention provides polynucleotides encoding the phytoene desaturase enzyme from Nicotiana species and numerous derivatives thereof. Specifically, the invention provides, in purified form, polynucleotides encoding the phytoene desaturase of *Nicotiana benthamiana*. Additionally, the invention provides polynucleotides encoding tomato (*Lycopersicon esculentum*) phytoene synthase and phytoene desaturase. The phytoene synthase and phytoene desaturase encoding polynucleotides described herein may be used to produce inhibitory RNAs specific for phytoene synthase and phytoene desaturase genes from a variety of plant species. The phytoene synthase and phytoene desaturase inhibitory RNA are preferably produced by transcription of phytoene synthase or phytoene desaturase inhibitory RNA encoding polynucleotides in functional combination with a promoter region.

The amino acid sequence of the various phytoene desaturase and the phytoene synthase enzymes described herein and the naturally occurring polynucleotide sequences encoding these enzymes enable a person of ordinary skill in the art of molecular biology to design and construct a variety of related molecules having useful properties similar to these enzymes and the polynucleotides obtained directly from the cloning of the cDNAs encoding these enzymes. In the case of polynucleotides, the degeneracy of the genetic code permits the person of ordinary skill in the art to produce numerous different polynucleotides encoding the same polypeptide, i.e., isocoding polynucleotides. The precise polynucleotide sequence produced may be selected so as to optimize expression in a particular host cell type, taking into account factors affecting expression such as codon frequency, potential mRNA secondary structures, methylation, and the like. The invention also provides a variety of polypeptides having the same enzymatic activity as phytoene desaturase and phytoene synthase, but differing in one or more amino acid residues, so as to produce a phytoene desaturase and phytoene synthase variant polypeptides. Variant polypeptides may be produced and designed in a wide variety of ways. Phytoene desaturase and phytoene synthase variants may be produced and designed by introducing mutations (either random or by design) into a polynucleotide sequence encoding the enzyme, transforming the mutated enzyme encoding polynucleotide (operably linked to a suitable promoter) into a host cell, and subsequently assaying the host cell for the expression of the desired enzymatic activity. The identity of mutations in Srf I encoding polynucleotides introduced randomly, may be determined by sequencing the polynucleotide encoding the enzyme.

The invention also provides for the recombinant DNA expression of phytoene desaturase adn phytoene synthase (as well as variants thereof). The recombinant expression of these enzyme may be achieved through standard recombinant DNA expression technology. Suitable recombinant DNA expression technology can be found, among other places, in Goeddel, et al., *Gene Expression Technology: Methods in Enzymology Volume* 185 Academic Press, San Diego (1991). The enzyme may be expressed in a wide range of host cells, including both eukaryotic and prokaryotic host cells. One advantage of providing the subject enzymes by recombinant DNA methodology is the production of increased amounts of enzyme from reduced amounts of cellular material.

Another advantage of the recombinant production of the enzymes is the ability to produce the enzyme free of certain contaminants. Phytoene synthase and phytoene desaturase (and variants thereof) produced by recombinant DNA techniques may be purified by procedures similar to the procedures described herein for the purification of the non-recombinant enzyme. Guidance in devising and modifying enzyme purification procedures can be found, among other places in Deutscher *Guide to Protein Purification Methods in Enzymology—Volume* 182) Academic Press, San Diego (1990), Scopes *Protein Purification: Principles and Practice* 3rd edition Springer-Verlag, N.Y. (1993), and the like.

The invention may be better understood by referring to the following examples. The following examples are offered for the purpose of illustrating the invention and should not be interpreted as a limitation of the invention.

EXAMPLES

Example 1

Isolation of Tomato Mosaic Virus cDNA

An 861 bp fragment (5524–6384) from the tomato mosaic virus (fruit necrosis strain F; ToMV-F) containing the putative coat protein subgenomic promoter, coat protein gene, and the 3' end was isolated by PCR using ToMV primers 5' CTCGCAAAGTTTCGAACCAAATCCTC 3' (SEQ ID NO: 1) (upstream) and 5' CGGGGTACCTGGGCCCCAAC-CGGGGGTTCCGGGGG3' (SEQ ID NO:2) (downstream) and subcloned into the HincII site of pBluescript KS–. A hybrid virus consisting of TMV-U1 and ToMV-F was constructed by swapping an 874-bp XhoI-KpnI ToMV fragment into pBGC152 (Kumagai, et al. *Proc. Natl. Acad. Sci USA,* 90:427–430 (1993)), creating plasmid TTO1. The inserted fragment was verified by dideoxynucleotide sequencing. A unique AvrII site was inserted downstream of the XhoI site in TTO1 by PCR mutagenesis, creating plasmid TTO1A, using the following oligonucleotides:
5' TCCTCGAGCCTAGGCTCGCAAAGTTTC-GAACCAAATCCTCA 3' (SEQ ID NO:3) (upstream),
5' CGGGGTACCTGGGCCCCAACCGGGGGT-TCCGGGGG 3' (SEQ ID NO:2) (downstream).

Example 2

Isolation of a cDNA Encoding Tomato Phytoene Synthase and a Partial cDNA Encoding Tomato Phytoene Desaturase Partial cDNAs were isolated from ripening tomato fruit RNA by polymerase chain reaction (PCR) using the following oligonucleotides: PSY, 5' TATGTATGGTGCAGAA-GAACAGAT 3' (SEQ ID NO:4) (upstream), 5' AGTC-GACTCTTCCTCTTCTGGCATC 3' (SEQ ID NO:5) (downstream); PDS, 5' TGCTCGAGTGTGTTCT-TCAGTTTTCTGTCA 3' (SEQ ID NO:6) (upstream), 5' AACTCGAGCGCTTTGATTTCTCCGAAGCTT 3' (SEQ ID NO: 7) (downstream). Approximately $3 \times 10^4$ colonies from a *Lycopersicon esculentum* cDNA library were screened by colony hybridization using a 32 P labelled tomato phytoene synthase PCR product. Hybridization was carried out at 42° C. for 48 h in 50% formamide, 5× SSC, 0.02 M phosphate buffer, 5× Denhart's solution, and 0.1 mg/ml sheared calf thymus DNA. Filters were washed at 65° C. in 0.1× SSC, 0.1% SDS prior to autoradiography. PCR products and the phyoene synthase cDNA clones were verified by dideoxynucleotide sequencing.

Example 3

DNA Sequencing and Computer Analysis

A 1.2 Kb PstI, BamHI fragment containing the phytoene synthase cDNA and a 0.7 Kb the partial phytoene desaturase cDNA was subcloned into pBluescript KS+ (Stratagene, La Jolla, Calif.). The nucleotide sequencing of KS+/PDS #38 and KS+/5'3'PSY was carried out by dideoxy termination using single stranded templates. Nucleotide sequence analysis and amino acid sequence comparisons were performed using PCGENE and DNA Inspector IIE programs.

Example 4

Construction of the Tomato Phytoene Synthase Expression Vector

A 1253 base pair XhoI fragment containing the tomato phytoene synthase cDNA was subcloned into TTO1. The vector TTO1/PSY+ (FIG. 1) contains the phytoene synthase cDNA (positive orientation) under the control of the TMV-U1 coat protein subgenomic promoter; while, the vector TTO1I/PSY—contains the phytoene synthase cDNA in the anti-sense orientation.

Example 5

Construction of a Viral Vector Containing a Partial Tomato Phytoene Destaturase cDNA An XhoI fragment containing the partial tomato phytoene desaturase cDNA was subcloned into TTO1. The vector TTO1A/PDS+ contains the phytoene desaturase cDNA (positive orientation) under the control of the TMV-U1 coat protein subgenomic promoter; while, the vector TTO1/PDS— contains the phytoene desaturase cDNA in the anti-sense orientation.

A partial cDNA encoding phytoene desaturase was isolated from *N. benthamiana* leaf RNA by RT-PCR using the following oligonucleotides: PDS, 5' GGCACTCAACTT-TATAAACC 3' (SEQ ID NO:8) (upstream), 5' CTTCAGTTTTCTGTCAAACC 3' (SEQ ID NO:9) (downstream) and verified by dideoxynucleotide sequencing.

Example 6

Transfection and Analysis of *N. benthamiana* [TTO1/PSY+, TTO1/PSY−. TTO1I/PDS700 +, TTO1I/PDS700 −]

Infectious RNAs from TTO1/PSY+ (FIG. 1), TTO1/PSY−, TTO1A/PDS+, TTO1/PDS− were prepared by in vitro transcription using SP6 DNA-dependent RNA polymerase and were used to mechanically inoculate *N. benthamiana* (Dawson, et al., *Adv. Virus Res.* 38:307 (1990)). The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. Plants transfected with TTO1/PSY+ showed at least a two fold increase in phytoene synthase activity over plants transfected with viral vector controls. Leaves from systemically infected TTO1/PSY+ plants developed a bright orange phenotype and accumulated high levels of phytoene (Table 1). The leaves and sepals from TTO1/PDS− plants developed a white bleaching phenotype similar to that seen with the herbicide norflurazon. The structure of the chloroplasts from TTO1/PSY+ and TTO1/PDS− transfected plants, when analyzed by transmission electron microscopy, appeared to be normal. Leaves from systemically infected TTO1A/PDS+ plants developed a bleaching white phenotype approximately one week later than leaves from anti-sense TTO1/PDS− plants and also accumulated high levels of phytoene.

Agarose gel electrophoresis of PCR cDNA isolated from virion RNA and Northern blot analysis of virion RNA indicate that the vectors are maintained in an extrachromosomal state and have not undergone any detectable intramolecular rearrangements.

TABLE I

Quantitation of phytoene leaves of *N. benthamiana* transfected with viral transcripts.

| Plant | | Phytoene μg/g FW | fold increase |
|---|---|---|---|
| *N. benthamiana* | — | 4.6 | 1 |
| *N. benthamiana*: | TTO1/PDS− | 234.8 | 51.0 |
| *N. benthamiana*: | Norflurozon | 339.8 | 73.9 |
| *N. benthamiana*: | TTO1/PSY+ | 52.4 | 11.4 |
| *N. benthamiana*: | TTO1/PSY− | 1.0 | 0.2 |

Example 7

Purification and Analysis of Phytoene From Transfected Plants

Phytoene was extracted in methanol and identified by its peak retention time and absorption spectra on a 25-cm Spherisorb ODS-1 5-μm column using acetonitrile/methanol/2-propanol (85:10:5) as a developing solvent at a flow rate of 1 ml/min. The phytoene isolated from systemically infected tissue had an identical retention time to phytoene from norflurozon treated plants. The phytoene peak from *N. benthamiana* transfected with TTO1/PSY+ had a characteristic optical absorbance maxima at 276, 285, and 298 nm. One week after inoculation, plants transfected with viral encoded phytoene synthase showed a hundred-fold increase in phytoene compared to the levels in noninfected plants as measured by HPLL separation of carotenoids. The carotenoids were extracted in methanol and identified by their peak retention time and absorption spectra on a 25-cm Spherisorb ODS-1 5-μm column using acetonitrile/methanol/2-propanol (85:10:5) as a developing solvent. The expression of sense (TTO1A/PDS+) and antisense (TTO1/PDS−) RNA to a partial phytoene desaturase in transfected plants inhibited the synthesis of colored carotenoids and caused the systemically infected leaves to develop a white phenotype. HPLC analysis of these plants revealed that they also accumulated phytoene high levels. The bleaching of leaves was reproduced in control plants treated with the herbicide norflurozon, a non-competitive inhibitor of phytoene desaturase.

Example 8

Isolation of a Partial cDNA Encoding N. benthamiana Phytoene Desaturase

A partial cDNA clone that encodes for N. benthamiana phytoene desaturase was isolated from young leaf tissue. Nucleotide sequence comparison of 369 bp in the corresponding regions between tomato and N. benthamiana phytoene desaturase indicate that they are 92% similar to each other (FIG. 2). Since the two plant genes have areas of high homology, cytoplasmic inhibition of the endogenous plant gene by viral-derived antisense RNA may occur through the formation of hybrid, double stranded RNA molecules. The down regulation of phytoene desaturase in plants transfected with TTO1A/PDS+ may be caused by direct interference during the translation of mRNA into protein or by duplexes formed between mRNA and viral-derived negative strand RNA, although the precise mechanism of action does not need to be known to carry out the invention.

Example 9

Construction of TTO1 and TTO1A Expression Vectors

An 861 bp fragment (5524–6384) from the tomato mosaic virus (fruit necrosis strain F; ToMV-F) containing the putative coat protein subgenomic promoter, coat protein gene, and the 3' end was isolated by PCR using ToMV primers 5' CTCGCAAAGTTTCGAACCAAATCCTC 3' (SEQ ID NO: 1) (upstream) and 5' CGGGGTACCTGGGCCCCAAC-CGGGGGTTCCGGGGG 3'(SEQ ID NO:2) (downstream) and subcloned into the HincII site of pBluescript KS−. A hybrid virus consisting of TMV-U1 and ToMV-F was constructed by swapping an 874-bp XhoI-KpnI ToMV fragment into pBGC152 (I. Pecker, et al., Proc. Natl. Acad. Sci. U.S.A., 89, 4962 (1992)), creating plasmid TTO1. The inserted fragment was verified by dideoxynucleotide sequencing. A unique AvrII site was inserted downstream of the XhoI site in TTO1 by PCR mutagenesis, creating plasmid TTO1A, using the following oligonucleotides:
5' TCCTCGAGCCTAGGCTCGCAAAGTTTC-GAACCAAATCCTCA 3' (upstream) (SEQ ID NO:3),
5' CGGGGTACCTGGGCCCCAACCGGGGGT-TCCGGGGG 3' (SEQ ID NO: 2) (downstream).

Example 10

Construction of TTO1/PDS−, TTO1A/PDS+

Using PCR mutagenesis a XhoI fragment, encoding tomato phyotene synthase was amplified from a Lycopersicon esculentum cDNA clone isolated from a ripening fruit cDNA library, and placed under the control of the TMV-U1 coat protein subgenomic promoter by subcloning into TTO1.

Example 11

Inhibition of the Expression of a Specific Endogenous Plant Gene (Phytoene Desaturase) using an RNA Viral Vector: Transfection and Analysis of N. benthamiana [TTO1/PDS−, TTO1A/PDS+

Infectious RNAs from TTO1A/PDS+, TTO1/PDS− were prepared by in vitro transcription using SP6 DNA-dependent RNA polymerase and were used to mechanically inoculate N. benthamiana. The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. The leaves and sepals from TTO1/PDS− plants developed a white bleaching phenotype similar to that seen with the herbicide norflurazon. The structure of the chloroplasts from TTO1/PDS− transfected plants, when analyzed by transmission electron microscopy, appeared to be normal. Leaves from systemically infected TTO1A/PDS+ plants developed a bleaching white phenotype approximately one week later than leaves from antisense TTO1/PDS plants and also accumulated high levels of phytoene.

Example 12

Inhibition of the Expression of a Specific Endogenous Plant Gene (Phytoene Synthase) Using an RNA Viral Vector: Transfection and Analysis of N. benthamiana [TTO1/PSY−]

Infectious RNAs from TTO1/PSY− were prepared by in vitro transcription using SP6 DNA-dependent RNA polymerase and were used to mechanically inoculate N. benthamiana. The hybrid viruses spread throughout all the non-inoculated upper leaves as verified by transmission electron microscopy, local lesion infectivity assay, and polymerase chain reaction (PCR) amplification. The viral symptoms consisted of distortion of systemic leaves, plant stunting, and mild chlorosis. Plants transfected with TTO1/PSY+ showed at least a two fold increase in phytoene synthase activity over plants transfected with viral vector controls (data not shown). Leaves from systemically infected TTO1/PSY+ plants developed a bright orange phenotype and accumulated high levels of phytoene (Table 1). The leaves from TTO1/PDS− plants developed a light bleaching phenotype. The structure of the chloroplasts from TTO1/PSY− when analyzed by transmission electron microscopy, appeared to be normal. Leaves from systemically infected TTO1A/PSY− plants did not accumulate phytoene.

Example 13

Isolation of a Partial cDNA Encoding N. benthamiana Phytoene Desaturase

A partial cDNA clone that encodes for N. benthamiana phytoene desaturase was isolated from young leaf tissue. Nucleotide sequence comparison of 380 bp in the corresponding regions between tomato and N. benthamiana phytoene desaturase indicate that they are 92% similar to each other (FIG. 2). Since the two plant genes have areas of high homology, cytoplasmic inhibition of the endogenous plant gene by viral-derived antisense RNA may occur through the formation of hybrid, double stranded RNA molecules. The down regulation of phytoene desaturase in plants transfected with TT01A/PDS+ may be caused by direct interference during the translation of mRNA into protein or by duplexes formed between mRNA and viral-derived negative strand RNA.

Example 15

Analysis of PDS mRNA in Nicotina Cells Producing Tomato PDS Derived Specific Anti-sense RNA Reverse Transcriptase PCR experiments measuring the presence or absence of detectable PDS mRNA transcripts in *N. benthamiana* cells containing TT01/PDS− (producing PDS anti-sense RNA) were performed. RNA was isolated from transfected plants by the method of Gailiano et al. The primers used to detect TT01/*L. esculeutum* were 5'TAATC-GATGATGATTCGGAGGCTAC3' (SEQ ID NO:12) (upstream) 5'GGCACTCAACTTTATAAACC3' (SEQ ID NO:13) (downstream). The primer used to detect *N. benthamiana* transcripts were 5'GGCACTCAACTT-TATAAACC3' (SEQ ID NO:8) (upstream) and 5' CTCCTT-TAATTGTACTGCCA3' (SEQ ID NO:12) (downstream). The PCR experiments were unable to detect endogenous PDS mRNA in the vector transfected plants, while the expected 452 bp anti-sense transcript could be detected. The 219 bp PDS mRNA could only be detected in the control, non-infected, *N. benthamiana* plants.

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

What is claimed is:

1. A genetic vector comprising:
   (a) a first viral subgenomic promoter operably joined to a first nucleic acid sequence that codes for a plant viral coat protein wherein the transcription of the first nucleic acid sequence is regulated by the first plant viral subgenomic promoter;
   (b) a second plant viral subgenomic promoter operably joined to a second nucleic acid sequence which codes for an anti-sense RNA or a co-suppressor RNA specific for a gene of interest in a plant wherein transcription of the second nucleic acid sequence is regulated by the second plant viral subgenomic promoter; and
   (c) an origin of replication that initiates replication of the genetic vector in the cytoplasm of a plant cell.

2. A genetic vector according to claim 1, wherein the genetic vector is derived from a RNA plant virus.

3. A genetic vector according to claim 2, wherein the RNA plant virus is a single stranded RNA plant virus.

4. A genetic vector according to claim 1, wherein the second viral subgenomic promoter is heterologous to the first viral subgenomic promoter.

5. A genetic vector according to claim 1, wherein at least one of the subgenomic promoters is derived from a tobamovirus.

6. A method of producing a plant cell having reduced expression of a gene of interest, the method comprising the steps of transfecting a plant cell with a genetic vector according to claim 1, wherein the nucleic acid sequence which codes for an anti-sense RNA or a co-suppressor RNA is specific for the gene of interest.

7. A method according to claim 6, wherein the genetic vector is derived from a RNA plant virus.

8. A method according to claim 7, wherein the genetic vector is derived from a plus-sense single stranded RNA plant virus.

9. A method according to claim 6, wherein the second viral subgenomic promoter is heterologous to the first viral subgenomic promoter.

10. A method according to claim 6, wherein at least one of the subgenomic promoters is derived from a tobamovirus.

11. A plant cell produced by the method of claim 6.

12. A plant cell according to claim 1, wherein the vector is derived from a RNA plant virus.

13. A plant cell according to claim 12, wherein the vector is derived from a plus-sense single stranded RNA plant virus.

14. A plant cell according to claim 11, wherein the second viral subgenomic promoter is heterologous to the first viral subgenomic promoter.

15. A plant cell according to claim 14 wherein at least one of the subgenomic promoters is derived from a tobamovirus.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:1:

CTCGCAAAGT TTCGAACCAA ATCCTC           26

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:2:

CGGGGTACCT GGGCCCCAAC CGGGGGTTCC GGGGG           35

(2) INFORMATION FOR SEQ ID NO:3:

(i) SEQUENCE CHARACTERISTICS:
      (A) LENGTH: 41 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:3:

TCCTCGAGCC TAGGCTCGCA AAGTTTCGAA CCAAATCCTC A           41

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

TATGTATGGT GCAGAAGAAC AGAT                                                      24

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

AGTCGACTCT TCCTCTTCTG GCATC                                                 25

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

TGCTCGAGTG TGTTCTTCAG TTTTCTGTCA                                    30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

AACTCGAGCG CTTTGATTTC TCCGAAGCTT                                    30

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

GGCACTCAAC TTTATAAACC                                                          20

(2) INFORMATION FOR SEQ ID NO:9:

(i) SEQUENCE CHARACTERISTICS:
        (A) LENGTH: 20 base pairs (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:9:

CTTCAGTTTT CTGTCAAACC                                              20

(2) INFORMATION FOR SEQ ID NO:10:

(i) SEQUENCE CHARACTERISTICS:
           (A) LENGTH: 114 base pairs
           (B) TYPE: nucleic acid
           (C) STRANDEDNESS: unknown
           (D) TOPOLOGY: unknown (ii) MOLECULE TYPE: DNA (genomic)

(ix) FEATURE:
           (A) NAME/KEY: CDS
           (B) LOCATION: 28..114

(xi) SEQUENCE DESCRIPTION: SEQ ID NO:10:

GTTTTAAATA CGCTCGAGGT TTTAAAT ATG TCT GTT GCC TTG TTA TGG GTT        51
                             Met Ser Val Ala Leu Leu Trp Val
                              1               5

GTT TCT CCT TGT GAC GTC TCA AAT GGG ACA AGT TTC ATG GAA TCA GTC     99
Val Ser Pro Cys Asp Val Ser Asn Gly Thr Ser Phe Met Glu Ser Val
         10                  15                  20

CGG GAG GGA AAC CGT                                                114
Arg Glu Gly Asn Arg
 25

(2) INFORMATION FOR SEQ ID NO:11:

(i) SEQUENCE CHARACTERISTICS:
           (A) LENGTH: 29 amino acids
           (B) TYPE: amino acid
           (D) TOPOLOGY: linear (ii) MOLECULE TYPE: protein (xi) SEQUENCE DESCRIPTION: SEQ ID NO:11:

Met Ser Val Ala Leu Leu Trp Val Val Ser Pro Cys Asp Val Ser Asn
 1               5                  10                  15

Gly Thr Ser Phe Met Glu Ser Val Arg Glu Gly Asn Arg
                 20                  25

(2) INFORMATION FOR SEQ ID NO:12:

(i) SEQUENCE CHARACTERISTICS:
           (A) LENGTH: 25 base pairs
           (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:12:

TAATCGATGA TGATTCGGAG GCTAC                                        25

(2) INFORMATION FOR SEQ ID NO:13:

(i) SEQUENCE CHARACTERISTICS:
           (A) LENGTH: 20 base pairs
           (B) TYPE: nucleic acid
           (C) STRANDEDNESS: unknown
           (D) TOPOLOGY: unknown

```
        (ii) MOLECULE TYPE: DNA (genomic)

(xi) SEQUENCE DESCRIPTION: SEQ ID NO:13:

CTCCTTTAAT TGTACTGCCA                                                  20

(2) INFORMATION FOR SEQ ID NO:14:

(i) SEQUENCE CHARACTERISTICS:
           (A) LENGTH: 380 base pairs
           (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:14:

ATAAACCCTG ACGAGCTTTC GATGCAGTGC ATCTTGATTG CTTTGAACAG ATTTCTTCAG       60

GAGAAACATG GTTCAAAAAT GGCCTTTTTA GATGGTAACC CTCCTGAGAG ACTTTGCATG      120

CCGATTGTGG AACATATTGA GTCAAAAGGT GGCCAAGTCA GACTAAACTC ACGAATAAAA      180

AAGATCGAGC TGAATGAGGA TGGAAGTGTC AAATGTTTTA TACAGAATAA TGGCAGTACA      240

ATTAAAGGAG ATGCTTTTGT GTTTGCCACT CCAGTGGATA TCTTGAAGCT TCTTTTGCCT      300

GAAGACTGGA AAGAGATCCC ATATTTCCAA AAGTTGGAGA AGCTAGTGGG AGTTCCTGTG      360

ATAAATGTCC ATATATGGTT                                                 380

(2) INFORMATION FOR SEQ ID NO:15:

(i) SEQUENCE CHARACTERISTICS:
           (A) LENGTH: 380 base pairs
           (B) TYPE: nucleic acid
           (C) STRANDEDNESS: unknown
           (D) TOPOLOGY: unknown (ii) MOLECULE TYPE: DNA (genomic)

(xi) SEQUENCE DESCRIPTION: SEQ ID NO:15:

ATAAACCCTG ACGAACTTTC AATGCAGTGC ATTTTGATCG CATTGAACAG GTTTCTTCAG       60

GAGAAACATG GTTCAAAAAT GGCCTTTTTA GATGGTAATC CTCCTGAGAG ACTTTGCATG      120

CCGATTGTTG AACACATTGA GTCAAAAGGT GGCCAAGTCA GACTGAACTC ACGAATAAAA      180

AAGATTGAGC TGAATGAGGA TGGAAGTGTC AAGAGTTTTA TACTGAGTGA CGGTAGTGCA      240

ATCGAGGGAG ATGCTTTTGT GTTTGCCGCT CCAGTGGATA TTTTCAAGCT TCTATTGCCT      300

GAAGACTGGA AAGAGATTCC ATATTTCCAA AAGTTGGAGA AGTTAGTCGG AGTACCTGTG      360

ATAAATGTAC ATATATGGTT                                                 380
```